United States Patent [19]

Okano et al.

[11] Patent Number: 4,584,275
[45] Date of Patent: Apr. 22, 1986

[54] INCUBATOR

[75] Inventors: Shinichi Okano; Takashi Koizumi; Tadashi Uekusa, all of Kanagawa, Japan

[73] Assignee: Fuji Photo Film Co., Ltd., Kanagawa, Japan

[21] Appl. No.: 403,380

[22] Filed: Jul. 30, 1982

[30] Foreign Application Priority Data

Jul. 31, 1981 [JP] Japan ................. 56-119355

[51] Int. Cl.⁴ ............ C12M 1/38; C12M 1/34; G01N 21/00
[52] U.S. Cl. .............................. 435/290; 435/291; 435/808; 435/809; 422/63; 422/65; 436/46
[58] Field of Search ........... 435/287, 288, 289, 290, 435/291, 808, 809; 422/65, 63, 64; 119/35, 37; 198/472, 580; 414/150, 156; 356/244; 436/46

[56] References Cited

U.S. PATENT DOCUMENTS

| | | | |
|---|---|---|---|
| 3,221,781 | 12/1965 | Forsström | 198/472 X |
| 3,451,564 | 6/1969 | Haas | 198/472 X |
| 3,654,091 | 4/1972 | Binnings et al. | 435/809 X |
| 3,809,208 | 5/1974 | Shields | 198/580 X |
| 4,067,694 | 1/1978 | Blakely et al. | 422/63 |
| 4,152,390 | 5/1979 | Nosco et al. | 422/65 X |
| 4,219,529 | 8/1980 | Tersteeg et al. | 422/65 |
| 4,224,032 | 9/1980 | Glover et al. | 435/809 X |
| 4,265,855 | 5/1981 | Mandle et al. | 422/63 X |
| 4,296,069 | 10/1981 | Smith et al. | 422/65 X |
| 4,296,070 | 10/1981 | Montalto et al. | 422/65 |
| 4,298,571 | 11/1981 | DiFulvio et al. | 422/65 |
| 4,303,611 | 12/1981 | Jessop | 422/65 |
| 4,384,193 | 5/1983 | Kledzik et al. | 435/809 |

FOREIGN PATENT DOCUMENTS 2755334 6/1978 Fed. Rep. of Germany ...... 356/244

*Primary Examiner*—Robert J. Warden
*Assistant Examiner*—Randall E. Deck
*Attorney, Agent, or Firm*—Sughrue, Mion, Zinn, Macpeak & Seas

[57] ABSTRACT

An incubator is provided with an inlet, a measurement station and an outlet for chemical analysis slides, and a number of levers or pushing devices for stepwisely circulating the slides through the apparatus. The device is useful for uniformly incubating a plurality of chemical analysis slides or the like according to a continuous, rather than batch, process.

20 Claims, 14 Drawing Figures

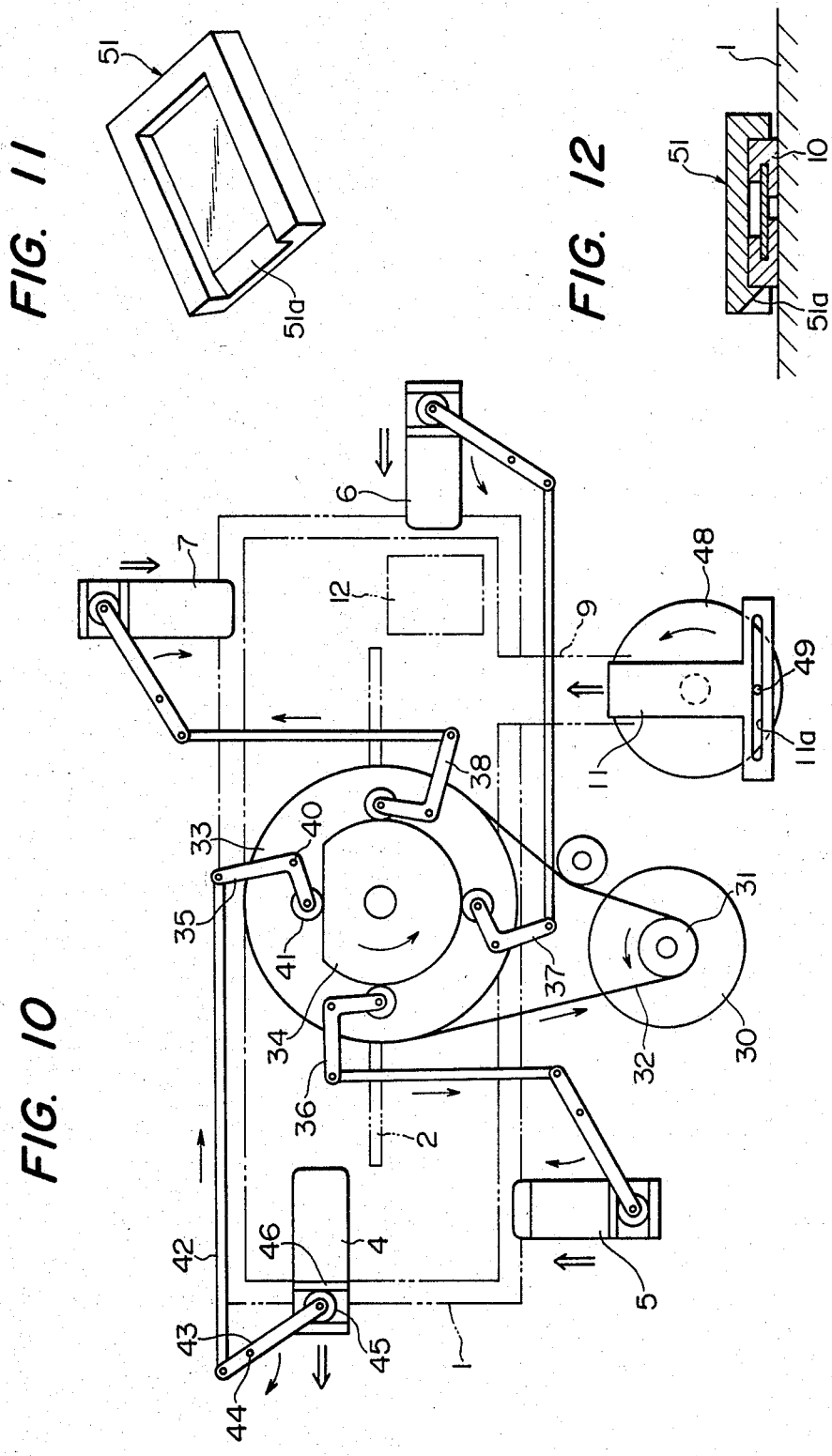

INCUBATOR

BACKGROUND OF THE INVENTION

This invention relates to devices for continuously incubating chemical analysis measurement units, and more particularly to an incubator which is employed in a clinical chemical examination system for performing quantitative analysis of a particular component included in a liquid specimen or body fluid such as blood or urine.

In present medical treatment, clinical chemical examination is essential for correct diagnosis and suitable medical care. Examination is carried out according to an enzyme measurement method in which an enzyme is used to measure a stroma; an immunity measurement method in which an antigen antibody reaction is utilized to quantitatively measure the antigen and antibody, and/or a method measuring the activity of non-organic ions in the body fluid.

In the immunity measurement method, the antigen and antibody are marked by some means, to quantitatively trace the antigen and antibody reaction. The marking may be effected with an enzyme, red corpuscle, bacteriophage, fluorescent material, radioactive isotope or special metal compound.

Measurement principles employed in the enzyme measurement method and in the enzyme iummunity measurement method using a marked enzyme are grouped into the spectral measurement method, fluorescent method and the electrode method. In spectral measurement, the variation in the absorbancy of a stroma or product is subjected to colorimetric determination, and in the case when no coloring reaction takes place with the stroma, a suitable coloring reagent which colors with the stroma or product is used. The fluorescent method is used in the case where a product of the enzyme reaction is a fluorescent material, and the sensitivity of this method is generally 100 to 1,000 times that of the spectral measurement method. In the electrode method, the variation of hydrogen ions caused by a hydrolysis reaction is measured, or the amount of oxygen in a liquid specimen changed by an oxygen reduction reaction is measured with an oxygen electrode. The enzyme measurement and the enzyme immunity measurement methods should be suitably selected according to the object to be measured.

In the enzyme measurement method, for instance, separated blood plasma, a dilute solution and an enzyme solution are poured into a cell, and are subjected to enzyme reaction in an incubator after being sufficiently mixed. The incubator is made up of a bath filled with water, and a heating source for maintaining the water bath at a predetermined temperature, for instance 37° C. The cell is incubated in the incubator for five to ten minutes. After incubation, light of a predetermined wavelength range, for instance from the near ultraviolet (190 to 400 nm) to the visible range (400 to 800 nm) is applied to the cell from one side thereof. The light passing through the cell and the solution is subjected to photo-electric conversion in a photo-detector and the stroma is quantitatively analyzed from its absorbancy. In the fluorescent method, a fluorophotometer is used to measure light from the product. In the electrode method, a pair of electrodes are inserted into a test tube, to measure the hydrogen ions or the like which are produced by the hydrolysis reaction.

However, the above-described method in which the cell or the test tube is used is disadvantageous in that a large quantity of liquid specimen is necessary, the operation is rather troublesome, measurement cannot be readily and quickly achieved and a number of liquid specimens cannot be continuously measured. In order to overcome these difficulties, a chemical analysis measurement unit has been proposed in which a measurement element such as a reagent layer is incorporated in a thin plastic frame (or container). One example of a chemical analysis measurement unit which is used in the spectral measurement method is described in the specification of Japanese Utility Model Application No. 41787/1980. The unit comprises a measurement element consisting of a transparent base layer, a reagent layer and a spread layer; a lower slide frame having a colorimetric hole at the center; and an upper slide frame having a liquid specimen dropping hole at the center, the peripheral portions of the two slide frames being welded together with the measurement element set between the two slide frames.

A chemical analysis measurement unit using a measurement element in the form of a dry multi-layer film is called a chemical analysis slide. In the case of the slide, a liquid specimen is dropped through a hole in the upper slide frame. After the liquid specimen has spread, the slide is incubated at 37° C. for six minutes so that a coloring reaction sufficiently takes place. Then, light is applied through the hole of the lower slide frame, so that light reflected from the reagent layer is subjected to colorimetric measurement to perform a quantitative analysis of a particular component.

The chemical analysis measurement unit using the frames can be used not only in the spectral measurement method, but also in the fluorescent method and the electrode method.

A unit for measuring the activity of non-organic ions in a liquid specimen, as disclosed by Japanese Patent Application Laid-Open No. 20499/1980, comprises a pair of solid electrodes; a porous material disposed between the solid electrodes; and a frame which incorporates these measuring elements and has a plurality of fluid insertion holes on one side. The frame further has terminals connected to the solid electrodes; and an electrometer is connected to the terminals. Under this condition, a reference body fluid is dropped through the frame's hole, while a liquid specimen is dropped through the other hole, thus forming a capillary bridge. The potential between the two electrodes is measured during incubation, to obtain the activities of such ions as $K^+$, $Na^+$, $Ca^+$, $Cl^-$ and $HCO_3^-$ in the liquid specimen.

For analytic measurement with high accuracy, the above-described chemical analysis measurement unit should be incubated at a temperature and for a period of time which is suitable for reaction conditions. However, almost all the conventional incubators employ baths. That is, an apparatus for readily and efficiently incubating chemical analysis measurement units having such thin frames has not been proposed in the art.

SUMMARY OF THE INVENTION

In view of the foregoing, an object of this invention is to provide an incubator which can continuously incubate a number of chemical analysis measurement units and which can be operated with ease.

A characteristic feature of the incubator according to the invention resides in that a circulated path is formed by alternately combining orthogonal straight grooves, and in that pushing levers are provided at the corners of the circulation path, so that chemical analysis measurement units are moved stepwise along the circulation path.

A chemical analysis slide is small in thickness, for instance about 1.5 mm. Therefore, adjacent slides may be overlapped when pushed with a pushing lever. Therefore, it is desirable that the chemical analysis slide be inserted in a carrier, so that the carrier is moved stepwise. In this case, the carrier is brought into close contact with the specimen side of the chemical analysis slide by its own weight, to thereby prevent the dissipation of moisture through a liquid specimen insertion hole formed in the specimen side thereof. On the other hand, the chemical analysis slide may be placed on the carrier.

If the chemical slide is relatively large in thickness, it is unnecessary to use such a carrier. In this case, it is preferable that the slide be brought into close contact with a thermostatic plate with the specimen side facing down, so that the evaporation of moisture is prevented. In the case where incubation is effected with the chemical analysis measurement unit set upside down, a measurement system such as a colorimeter is set above the thermostatic plate.

BRIEF DESCRIPTION OF THE DRAWINGS

FIG. 10 is a plan view showing a pushing lever drive device;

FIG. 11 is a perspective view showing another example of the carrier;

FIG. 12 is a sectional view showing the carrier of FIG. 11 in which a chemical analysis slide has been inserted;

DETAILED DESCRIPTION OF THE PREFERRED EMBODIMENTS

Figure 1:
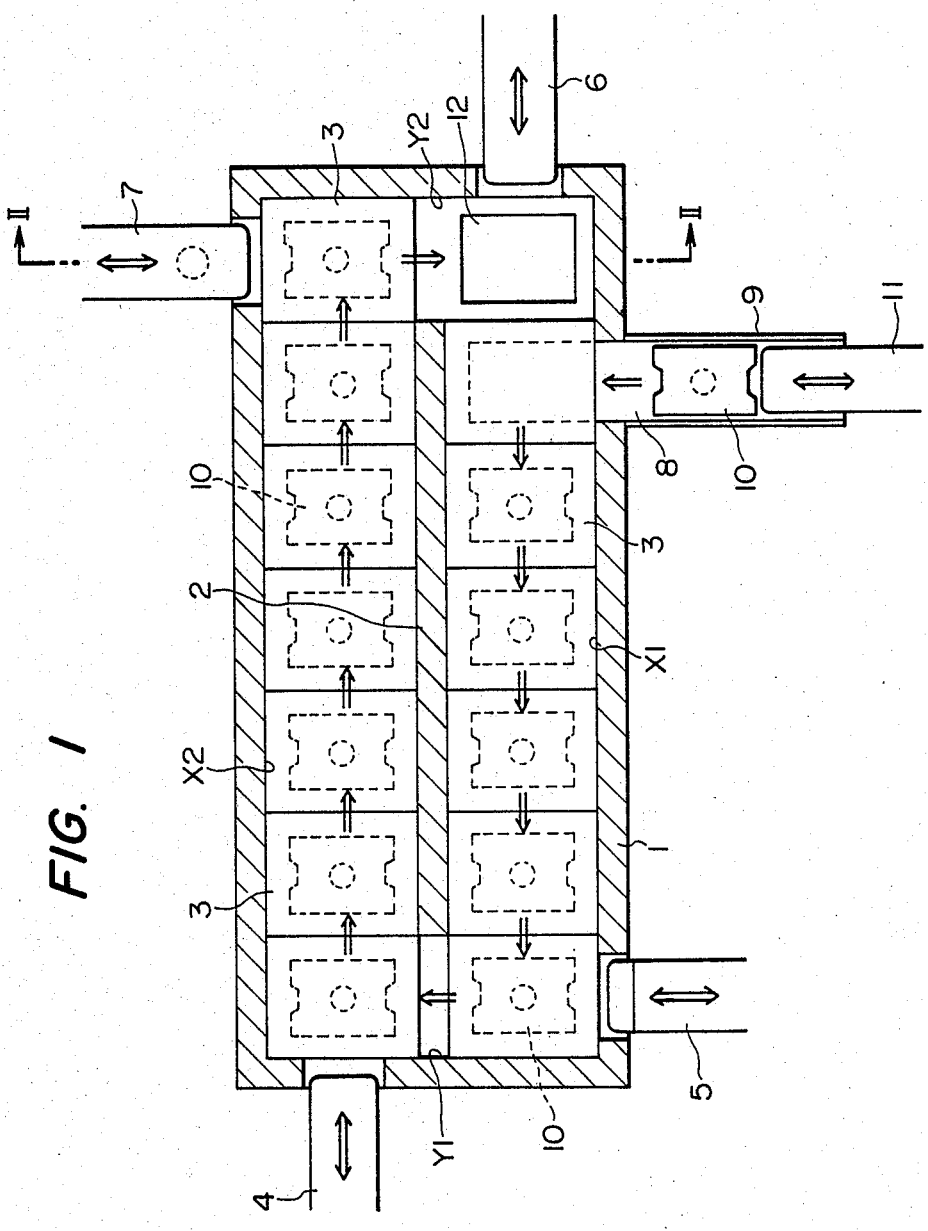
FIG. 1 is a sectional view showing a first embodiment of this invention.

As shown in FIG. 1, a heating plate is provided with a heater and a temperature detector, and is maintained at a predetermined temperature, for instance 37° C., according to reaction conditions. The heating plate 1 has straight grooves X1 and X2 and straight grooves Y1 and Y2 which are orthogonal to the former. These straight grooves X1, Y1, X2 and Y2 together form a circulation path. A partition wall 2 is formed between the straight grooves X1 and X2, so that the corners of carriers 3 sliding on the straight grooves X1 and X2 will not be caught by or engaged with one another; however, it is not always necessary to provide the partition wall 2.

Pushing levers 4, 5, 6 and 7 are provided at the corners of the circulation path, respectively, so that the carrier 3 at a corner may be moved by one frame, or two frames as the case may be.

A channel 9 is connected to an insertion inlet 8, and a chemical analysis slide 10 is placed in the channel. Body fluid is placed on the sample side of the slide 10. After the body fluid has been spread, the slide 10 is moved by the pushing lever 11, so that it is placed in a carrier 3.

The carrier 3 into which the chemical analysis slide 10 has been inserted, is moved to the left by one frame at a time along the straight groove X1 by the pushing lever 6 until it reaches the straight groove Y1. The carrier 3, which has reached the straight groove Y1, is then moved by the pushing lever 5 until it reaches the straight groove X2. The carrier 3 is further moved along the straight groove X2 by the lever 4 until it reaches the straight groove Y2. The carrier 3 is correctly positioned by the corner of the straight groove Y2, so that it may be subjected to colorimetric determination to perform a quantitative analysis of a particular component of the body fluid. After the colorimetric determination, the carrier 3 is moved to a discharge position by the pushing lever 7. A discharging outlet 12 is provided at the discharge position. When the carrier 3 reaches the outlet 12, only the slide 10 is allowed to drop into a container for receiving chemical analysis slides. The carrier 3, after discharging the slide 10, is pushed back to the inserting inlet 8 by the pushing lever 6.

The chemical analysis slide 10 is incubated at a predetermined temperature while being intermittently moved along the circulation path from the inserting inlet 8 to the measurement position. The period of incubation can be set to a desired value by controlling the timing of the operations of the pushing levers 4 through 7. For instance in the case where glycosidase is employed as an enzyme to measure the density of glycoside in the blood, it is suitable for the incubating period to be six minutes at 37° C.

The heating plate 1 is made of aluminum, which is excellent in thermal conductivity. The carrier 3 is made of a resin or metal which exhibits a small coefficient of friction.

Figure 2:
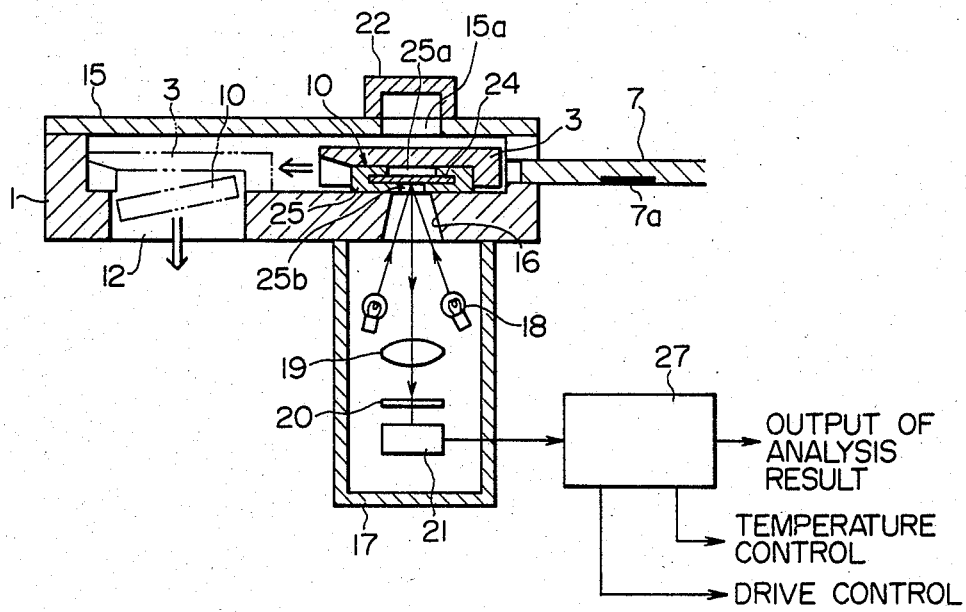
FIG. 2 is a sectional view taken along the line II—II of FIG. 1.

FIG. 2 shows the arrangement of an analysis/measurement section. An upper cover 15 is placed on the heating plate 1. The upper cover 15 is made of transparent glass or resin so that the operator can observe the movement of the carriers 3. In order to maintain the circulation path at a uniform temperature, it is desirable to provide a heater for the upper cover 15. If a heater is provided only for the upper cover 15 and not for the heating plate 1, it is possible to set the temperature of the heating plate 1 to a certain value using only heat radiated from the upper cover 15.

A hole 16 is formed in the heating plate 1 at the aforementioned measurement position. A dark box or enclosure 17 is provided below the hole 16. The dark box 17 incorporates an illuminating light source 18, a lens 19, a color filter 20 and a photo-detector 21. The upper cover 15 has a hoel 15a above the aforementioned hole 16. A dark box 22 is provided in such a manner as to surround the hole 15a.

The chemical analysis slide 10 is made up of a measurement element 24 which is obtained by forming reagent layers in a dry multi-layer film, and a frame 25 which receives the measurement element 24 and has an upper hole 25a, namely, a liquid specimen receiving hole, and a lower hole 25b, namely, a photometric hole. In the reagent layer, the reagent reacts with the liquid specimen, as a result of which coloring is effected to a density corresponding to a particular material of the liquid specimen. The degree of the coloring reaction depends on the incubation time, the amount of moisture and the amount of oxygen. Among these factors, the amount of moisture is most important; that is, it is essential that there be a sufficient amount of moisture during the coloring reaction. Since the amount of liquid specimen is very small, for instance 10 μl, the moisture dissipates through the hole 25a during incubation, as a result of which the coloring process may stop. On the other hand, no moisture dissipates through the hole 25b on the photometric side, because a base layer (or a transparent plastic film) closes the hole 25b.

As the carrier 3 is placed on the specimen side to close the hole 25a, the evaporation of moisture can be effectively prevented and the coloring reaction may be sufficiently effected. A layer of air is formed in the hole 25a; that is, a sufficient amount of oxygen is supplied for the reaction.

When the chemical analysis slide 10 is set upside down so that the specimen side faces downwardly, the specimen side is brought into close contact with the heating plate 1 by the weight of the carrier 3. In this case also, the evaporation of moisture can be prevented. In addition, it should be noted that the position of the box 17 is opposite to that of the dark box 22 in this case. If the chemical analysis slide 10 is set upside down when the carrier 3 is not used, then the specimen side is brought into close contact with the heating plate 1 by the weight of the slide 10, so that the evaporation of moisture can be prevented.

The chemical analysis slide 10 at the measurement position is illuminated by light from the light source 18. Light reflected from the reagent layer of the slide 10 advances through the hole 25b, the hole 16, the lens 19 and the color filter 20 to the photo-detector 21, where light of only a predetermined range of wavelengths is subjected to photo-electric conversion.

Figure 3:
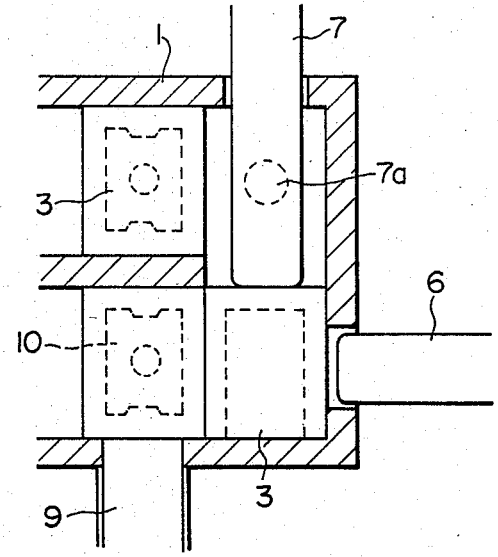
FIG. 3 is a sectional view showing a pushing lever.

When, after the colorimetric measurement, the pushing lever 7 is moved as shown in FIG. 3, the carrier 3 is moved to the outlet 12 and the chemical analysis slide 10 is discharged therethrough. While the lever 7 is moved as described above, light reflected from a white point 7a below the lever 7 is measured by the photo-detector 21. The white point is of titanium oxide or ceramic.

Figure 4:
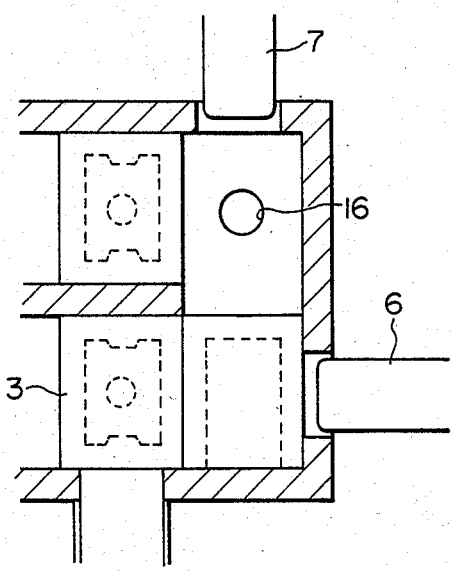
FIG. 4 is a sectional view showing a pushing lever which has been retracted.

When the pushing lever 7 is retracted as shown in FIG. 4, there is nothing over the hole 16. In this case, light reflected from the black interior of the dark box 22 is measured.

The dark box 22 is used as a black reference point, and its photometric output or reflection factor is 0%. The photo-metric output of the white reference point 7a is of a reflection factor of 100%. Therefore, when the reagent-layer is subjected to photometry by the detector using these outputs as reference levels, a correct reflection factor can be obtained from the output of the detector. The white reference point and the black reference point may be provided on the pushing lever 7 in such a manner that they are spaced from each other. In this case, pushing lever 7 would be pushed in two steps.

The output of the photo-detector 21 is applied to an analysis control unit 27, where quantitative analysis is carried out by referring to a preset standard curve, and the result thereof is output. Usually, the results of the analysis are printed out along with the chemical analysis slide number. The analysis control device is a microcomputer which carries out the analysis process, as well as temperature and drive control.

Figure 5:
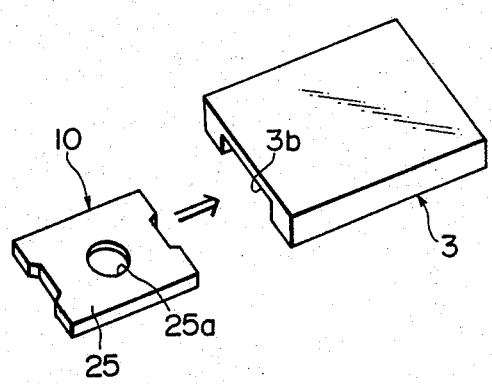
FIGS. 5 and 6 are perspective views showing one example of a carrier.
Figure 6:
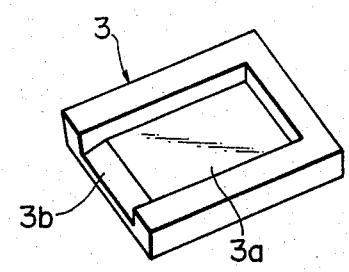

FIGS. 5 and 6 show the aforementioned carrier 3 in more detail. The carrier 3 has a recess 3a with an inlet 3b at the bottom thereof, so that the chemical analysis slide 10 can be inserted into the recess 3a via the inlet 3b. The inlet 3b is inclined so that the slide 10 can be smoothly inserted into the recess 3a.

Figure 7:
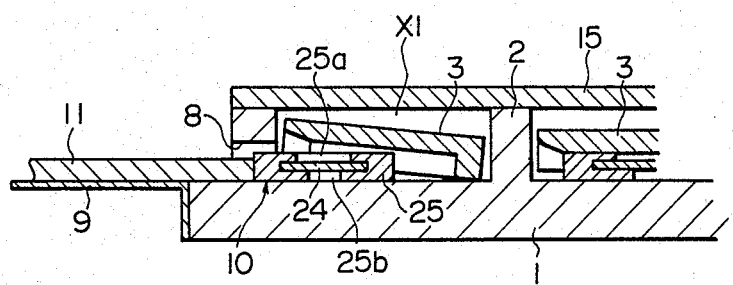
FIGS. 7 through 9 are sectional views for describing the operation of the pushing levers.

FIG. 7 shows the insertion of the chemical analysis slide into the carrier. As the pushing lever 11 is pushed, the chemical analysis slide 10 is pushed into the recess 3a of the carrier 3 thereby. The height of the recess 3a is smaller than the thickness of the slide 10. Therefore, at the start of the insertion, the inlet 3b of the carrier 3 is raised. When the slide 10 has been completely inserted into the recess 3a, the carrier 3 is positioned on the chemical analysis slide 10; i.e., it is brought into close contact with the specimen side thereof. Since the end portion of the pushing lever 11 must move into the inlet 3b of the carrier 3, it must be made relatively thin.

Figure 8:
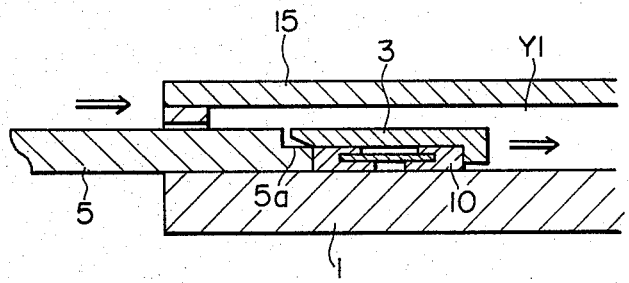

FIG. 8 illustrates the operation of the pushing lever 5. The pushing lever 5 has a step 5a at the end thereof. The lever 5 pushes both the carrier 3 and the slide 10 until the latter moves along the straight groove Y1 by one frame.

Figure 9:
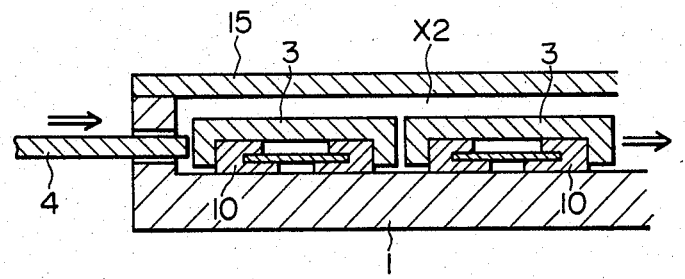

FIG. 9 shows the operation of the pushing lever 4. When the pushing lever 4 is advanced, all of the series of carriers 3 in the groove X2 are moved along the groove by one frame.

FIG. 10 shows a pushing-lever drive device. A pulley 31 is mounted on the output shaft of a motor 30. The rotation of the motor 30 is transmitted through the pulley 31 and a belt 32 to a pulley 33. A cam 34 is provided coaxially with the pulley 33. The cam 34 is substantially in the form of a semicircle obtained by cutting a portion of a circle. Four followers 35, 36, 37 and 38 are rockably provided in such a manner that they are in contact with the cam 34.

The followers are coupled to the pushing levers through identical mechanisms, respectively. Therefore, only the mechanism through which the follower 35 is coupled to the pushing lever 4 will be described. The follower 35 is pivotablly mounted on a shaft 40, and has a roller 41 at one end, which is in contact with the periphery of the cam 34. A connecting rod 42 is connected to the other end of the follower 35, so that the motion of the follower 35 is transmitted to a lever 43. The lever 43 is pivotablly mounted on a shaft 44, and a roller 45 is mounted on one end of the lever. The roller 45 is fitted in a U-shaped rail 46 provided in the pushing lever 4.

The cam 34 has a circular cam surface and a straight cam surface. When the straight cam surface of the cam 34 comes to the position of the follower 35 as the cam 34 is turned, the follower 35 is turned counterclockwise, and accordingly the lever 43 is turned counterclockwise through the connecting rod 42. As the lever 43 is turned counterclockwise, the pushing lever is moved to the right, thereby to shift carriers 3 along the groove X2 by one frame. As the cam 34 is further turned, the straight cam surface leaves the follower 35. Thereupon, the pushing lever 4 is moved to the left, thus retracting from the circulation path.

As the cam 34 turns, the pushing levers 4 through 7 are operated successively. That is, as the cam makes one revolution, all the carriers 3 in the circulation path are advanced by one frame.

The pushing lever 11 is provided to insert chemical analysis slides 10 into the carrier 3 as described above. The pushing lever 11 is moved back and forth by means of a pin 49 embedded in a cam 48 and engaged with an elongated hole 11a cut in the lever 11. The cam 48 is synchronous with the aforementioned cam 34, and therefore the lever 11 is moved forwardly while the pushing lever 6 is maintained stopped.

In the above-described embodiment, no carrier is provided at one corner, and the pushing levers 4 through 7 are operated successively so that the empty corner is shifted forwardly. Two empty corners may be provided, at the upper left corner and a the lower right corner. In this case, the pushing levers 5 and 7 may be operated simultaneously, and the pushing levers 4 and 6 may likewise be operated at the same time.

In the above-described embodiment, the pushing levers 4 through 7 are operated by a cam mechanism; however, if solenoids are provided for the levers, respectively, the levers can be driven independently. Furthermore, if a valve plate is provided for the discharging outlet 12, a chemical analysis slide 10 can be circulated plural times by operating the valve plate. The latter method is effective in simultaneously incubating chemical analysis slides which have different incubation times.

FIGS. 11 and 12 show one modification of the carrier which is designed so as to prevent the vibration of the chemical analysis slide therein. A pawl 51a is formed in the inlet of the carrier 51 as shown in FIG. 12, to prevent relative movement between the chemical analysis slide 10 and the carrier 51.

Figure 13:
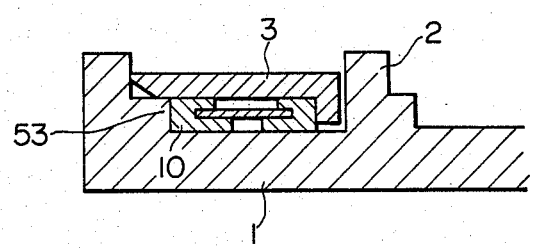
FIG. 13 is a sectional view showing another embodiment of the invention in which the straight grooves have been modified.

FIG. 13 shows another embodiment of the invention. In this embodiment, a step 53 is formed along the straight grooves. The inlet side of the carrier 3 is placed on the step 53, while the side of the chemical analysis slide 10 is placed in contact with the side wall of the step 53.

Figure 14:
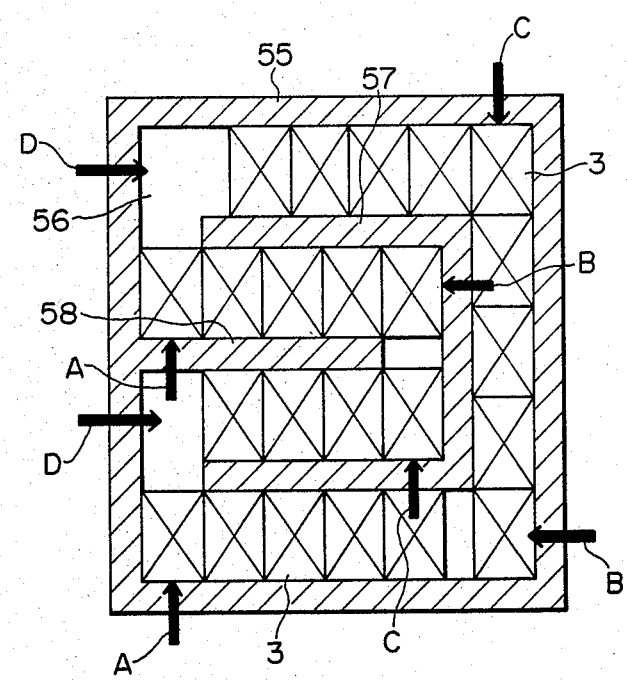
FIG. 14 is a sectional view showing another embodiment of the invention, which has a maze-like circulation path.

FIG. 14 illustrates another embodiment of the invention, in which the circulation path is in the form of a maze. In this case, a plurality of partition walls 57 and 58 are formed in the recess 56 of the heating plate 55. The carriers in the circulation path are advanced by one frame by successively operating pushing levers A through D. The inserting inlets and the discharging outlets may be provided at any desired positions.

As is apparent from the above description, according to the invention, a circulation path is formed on the heating plate, and the chemical analysis slides are inserted into the circulation path and are moved stepwise along the circulation path. Therefore, a number of chemical analysis measurement units can be continuously and efficiently incubated.

Even when the heating plate is somewhat non-uniform in temperature distribution, the chemical analysis measurement units can be uniformly incubated as they are moved on the heating plate. Furthermore, since the chemical analysis measurement units are intermittently moved from the inserting inlet to the discharging outlet, the incubation time is maintained constant.

What is claimed is:
1. An incubator, comprising:
an enclosure defining a circulation path for guiding a plurality of chemical analysis units each carrying a material to be analyzed, said enclosure including an insertion inlet through which said chemical analysis measurement units are inserted into said circulation path at an insertion position of said circulation path, and a discharging outlet through which said chemical analysis measurement units are discharged at a discharge position of said circulation path;
means for maintaining said chemical analysis measurement units at a controlled temperature in said circulation path;
a plurality of carrier members each having a recess in a lower surface thereof for receiving a respective one of said chemical analysis units, said carrier members each comprising a box-shaped carrier having a sidewall portion and a top portion defining said recess, said sidewall portion having an inlet on one side thereof, said chemical analysis measurement units being inserted into said carriers through each said inlet; and
a plurality of pushing levers for moving said chemical analysis measurement units through the circulation path from said inlet to said outlet.

2. An incubator as claimed in claim 1, wherein said circulation path is rectangular.

3. An incubator as claimed in claim 2, said circulation path having four corners, a pushing lever being provided at each said corner, respectively, said pushing levers being operated sequentially.

4. An incubator as claimed in claim 3, further including insertion means for supplying chemical analysis measurement units through said insertion inlet, said insertion means operating synchronously with said pushing levers, whereby chemical analysis measurement units are continuously circulated from said insertion inlet to said discharging outlet.

5. An incubator as claimed in claim 3, further including cam and follower means for sequentially operating said pushing levers, and links connecting said followers to each said lever.

6. An incubator as claimed in claim 1, said circulation path being composed of a plurality of orthogonal, straight grooves.

7. An incubator as claimed in claim 1, further including valve means for selectively covering said discharging outlet.

8. An incubator as claimed in claim 1, wherein said sidewall portions of said carriers have a height less than the thickness of said units, whereby each said carrier is brought into close contact with a specimen side of said chemical analysis measurement unit by the weight of said carrier, to cover a liquid speciment introduction hole of said unit.

9. An incubator as claimed in claim 1, said carrier inlet being beveled.

10. An incubator as claimed in claim 1, said carrier inlet including a pawl for engaging a back side of said unit.

11. An incubator as claimed in claim 1, said circulation path being in the form of a maze.

12. An incubator, comprising:
an enclosure defining a circulation path for guiding a plurality of chemical analysis measurement units;
means for maintaining said chemical analysis measurement units at a controlled temperature in said circulation path;
a plurality of carrier members each having a recess for receiving a respective one of said chemical analysis units, each said carrier member comprising a box-shaped carrier having a sidewall portion and a top portion defining said recess, said sidewall portion having an inlet on one side thereof, said chemical analysis measurement units being inserted into said carriers through each said inlet;

a plurality of pushing levers for moving said chemical analysis measurement units through said circulation path, said plurality of pushing levers including at least first and second levers for pushing said chemical analysis measurement units in first and second orthogonal directions;

rotatable cam means having a camming surface, said camming surface being substantially circular except for a single flat portion thereof; and first and second cam follower means each abutting said camming surface and controlling movement of said first and second levers, respectively, each cam follower means causing its respective lever to extend into said circulation path for pushing said chemical analysis measurement units when its respective cam follower means contacts said flat portion of said camming surface, said first and second cam follower means being separated by approximately 90° around the periphery of said camming surface.

13. An incubator, comprising:

an enclosure defining a circulation path for guiding a plurality of chemical analysis measurement units each carrying material to be analyzed;

means for maintaining said chemical analysis measurement units at a controlled temperature in said circulation path;

a plurality of carrier members each having a recess for receiving a respective one of said chemical analysis units, said carrier members each comprising a box-shaped carrier having a sidewall portion and a top portion defining said recess, said sidewall portion having an inlet of one side thereof, said chemical analysis measurement units being inserted into said carriers through each said inlet;

optical means for performing an analysis measurement on each side material in accordance with light reflected from said material when its respective chemical analysis unit is at a measurement position; and a plurality of pushing levers for moving said chemical analysis measurement units through said circulation path, at least one of said levers extending into and out of said measurement position and having a surface facing said optical means, said surface having thereon first means for providing to said optical means a first reference level of reflection when said lever is extended into said measurement position.

14. An incubator as claimed in claim 13, further comprising second means disposed on a side of said measurement position opposite said optical means for providing a second reference level of reflection to said optical means when no chemical analsyis measurement unit is presently in said measurement position and said at least one lever is not extended into said measurement position.

15. An incubator as claimed in claim 14, wherein said first means provides a relatively high reference level of reflection and said second means provides a relatively low reference level of reflection.

16. An incubator, comprising:

an enclosure defining a circulation path for guiding a plurality of chemical analysis units each carrying a material to be analyzed, said enclosure including an insertion inlet through which said chemical analysis measurement units are inserted into said circulation path at an insertion position of said circulation path, and a discharging outlet through which said chemical analysis measurement units are discharged at a discharge position of said circulation path;

means for maintaining said chemical analysis measurement units at a controlled temperature in said circulation path;

a plurality of carrier members each having a recess in a lower surface thereof for receiving a respective one of said chemical analysis units, each said carrier member being larger than said discharging outlet and each comprising a box-shaped carrier having a sidewall portion and a top portion defining said recess, said sidewall portion having an inlet on one side thereof, said chemical analysis measurement units being inserted into said carriers through each said inlet; and a plurality of pushing levers for moving said chemical analysis measurement units through said circulation path from said inlet to said outlet by pushing said carrier members, said chemical analysis measurement units falling through said discharge opening upon reaching said discharge position, and the resulting empty carrier member being advanced to said insertion position for receiving a further chemical analysis measurement unit.

17. An incubator as claimed in claim 16, wherein said discharge opening is formed in a lower surface of said enclosure along which lower surface said chemical analysis measurement units are moved in sliding contact through said circulation path, each said carrier member including a top surface for covering a respective chemical analysis measurement unit and at least two side surfaces extending downward on opposite sides of said chemical analysis measurement units, said side surfaces extending downward for a distance less than the thickness of said chemical analysis measurement units, whereby said carrier member is out of contact with said enclosure lower surface and the weight of said carrier member is supported by an upper peripheral surface of said chemical analysis measurement unit.

18. An incubator as claimed in claim 17, wherein said circulation path is defined by a groove formed in said enclosure, said groove having a lower surface comprising said lower surface of said enclosure along which said chemical analysis measurement units are moved in sliding contact, each said chemical analysis measurement unit falling into said groove when inserted at said insertion inlet.

19. An incubator as claimed in claim 18, wherein each said carrier member includes a beveled surface on a side thereof facing said insertion inlet when said each carrier member is at said insertion position, said chemcial analysis measurement unit being urged against said beveled surface to raise said carrier member upon insertion of said chemical analysis measurement unit.

20. An incubator as claimed in claim 16, wherein each said chemical analysis measurement unit comprises a slide for supporting said material to be analyzed and a frame for supporting said slide, said frame having a first aperture in a lower surface thereof for permitting optical analysis of said material to be analyzed and a second aperture in an upper surface thereof for receiving said material to be analyzed.

* * * * *